(12) United States Patent
Wilson

(10) Patent No.: US 8,052,639 B2
(45) Date of Patent: Nov. 8, 2011

(54) CLAMPLESS ANASTOMOTIC DEVICE

(76) Inventor: David B. Wilson, Grand Blanc, MI (US)

(*) Notice: Subject to any disclaimer, the term of this patent is extended or adjusted under 35 U.S.C. 154(b) by 176 days.

(21) Appl. No.: 12/099,650

(22) Filed: Apr. 8, 2008

(65) Prior Publication Data

US 2008/0255506 A1    Oct. 16, 2008

Related U.S. Application Data

(60) Provisional application No. 60/910,838, filed on Apr. 10, 2007.

(51) Int. Cl.
*A61M 29/00* (2006.01)

(52) U.S. Cl. .......... 604/103.07; 604/96.01; 604/103; 606/194

(58) Field of Classification Search ............ 604/97.01, 604/103, 103.1, 103.03, 103.09, 907, 915, 604/96.01, 103.07, 916; 606/200, 194
See application file for complete search history.

(56) References Cited

U.S. PATENT DOCUMENTS

| | | | |
|---|---|---|---|
| 4,610,662 A | 9/1986 | Weikl et al. | |
| 4,781,677 A | 11/1988 | Wilcox | |
| 4,976,710 A | 12/1990 | Mackin | |
| 5,019,042 A | 5/1991 | Sahota | |
| 5,135,474 A | 8/1992 | Swan et al. | |
| 5,167,628 A | 12/1992 | Boyles | |
| 5,222,966 A * | 6/1993 | Perkins et al. | 606/159 |
| 5,342,306 A | 8/1994 | Don Michael | |
| 5,571,167 A | 11/1996 | Maginot | |
| 5,599,307 A | 2/1997 | Bacher et al. | |
| 5,674,198 A | 10/1997 | Leone | |
| 5,693,014 A | 12/1997 | Abele et al. | |
| 5,797,946 A | 8/1998 | Chin | |
| 5,823,995 A | 10/1998 | Fitzmaurice et al. | |
| 6,010,480 A | 1/2000 | Abele et al. | |
| 6,045,531 A | 4/2000 | Davis | |
| 6,135,981 A | 10/2000 | Dyke | |
| 6,143,015 A | 11/2000 | Nobles | |
| 6,234,995 B1 | 5/2001 | Peacock, III | |
| 6,264,633 B1 | 7/2001 | Knorig | |
| 6,464,665 B1 | 10/2002 | Heuser | |
| 6,558,405 B1 | 5/2003 | McInnes | |
| 6,663,590 B2 | 12/2003 | Blatter | |
| 6,689,097 B2 | 2/2004 | Thramann | |
| 6,695,810 B2 * | 2/2004 | Peacock, III et al. | 604/99.04 |
| 6,712,831 B1 | 3/2004 | Kaplan et al. | |
| 7,122,019 B1 * | 10/2006 | Kesten et al. | 604/93.01 |
| 7,156,870 B2 | 1/2007 | Kashyap | |
| 2004/0215312 A1 * | 10/2004 | Andreas | 623/1.11 |
| 2005/0119682 A1 * | 6/2005 | Nguyen et al. | 606/194 |
| 2006/0041269 A1 * | 2/2006 | Horrigan | 606/198 |
| 2006/0106337 A1 * | 5/2006 | Blankenship | 604/103.06 |
| 2007/0005105 A1 | 1/2007 | Kusleika et al. | |
| 2007/0010868 A1 | 1/2007 | Ferren et al. | |
| 2007/0016133 A1 | 1/2007 | Pepper | |

* cited by examiner

*Primary Examiner* — Nicholas D Lucchesi
*Assistant Examiner* — Jenna Zhang
(74) *Attorney, Agent, or Firm* — Howard & Howard Attorneys PLLC

(57) ABSTRACT

Described is a medical device and method for allowing fenestration of the aortic wall while maintaining distal perfusion and preventing external bleeding. The device isolates a segment of the aortic wall from the flowing column of blood using a balloon mounted on a metal alloy strut assembly. The strut assembly expands radially from a collapsed, low-profile configuration when uncovered by a constraining outer sheath. Aortic blood flow is allowed through the flow passage thus contained by the strut assembly within the center of the balloon. The balloon is inflated to contact the aortic wall. The balloon contains a pocket shaped to allow aortic fenestration. The balloon contains radiopaque markers to facilitate orientation and positioning of the pocket within the aorta. Other embodiments using spaced balloons are also disclosed.

22 Claims, 9 Drawing Sheets

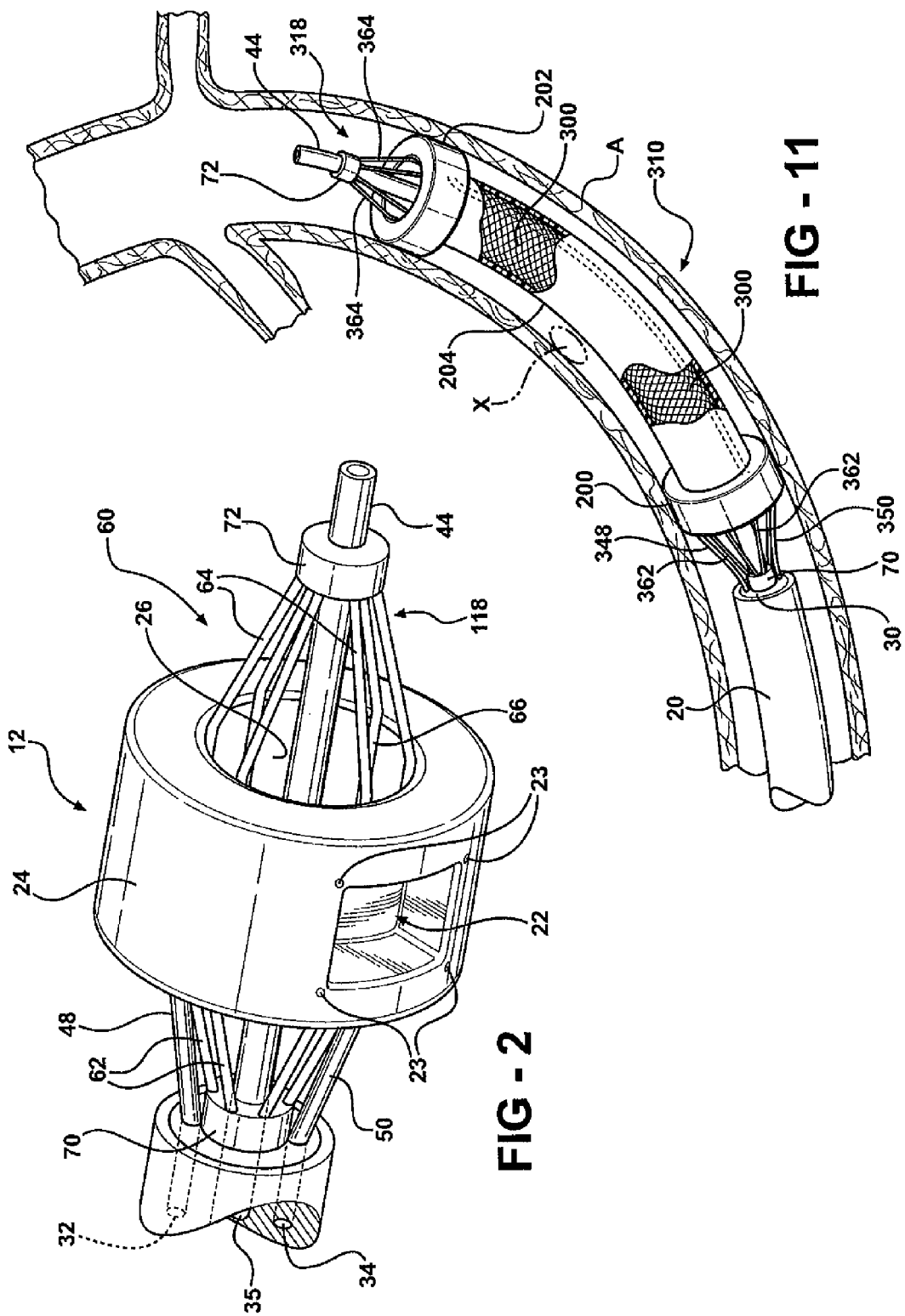

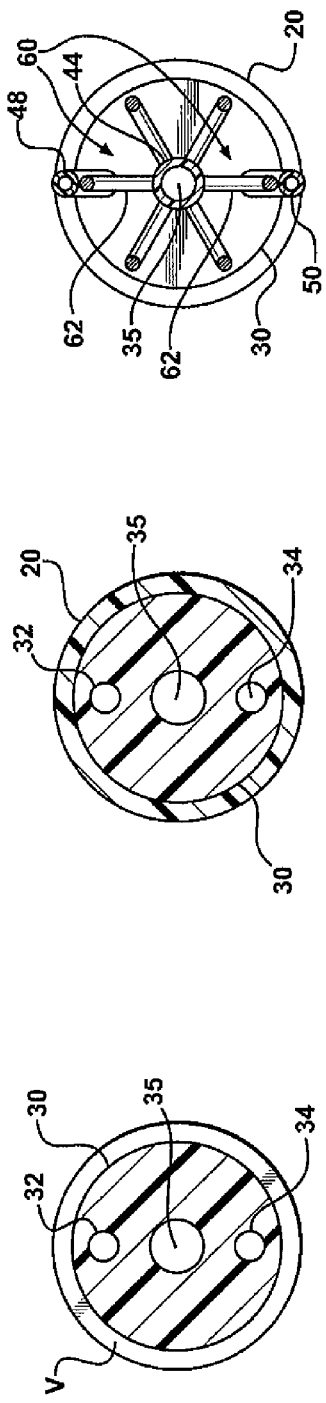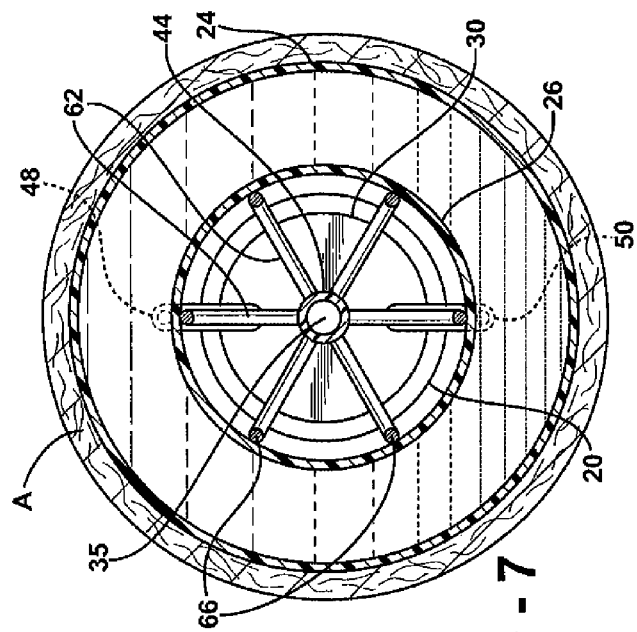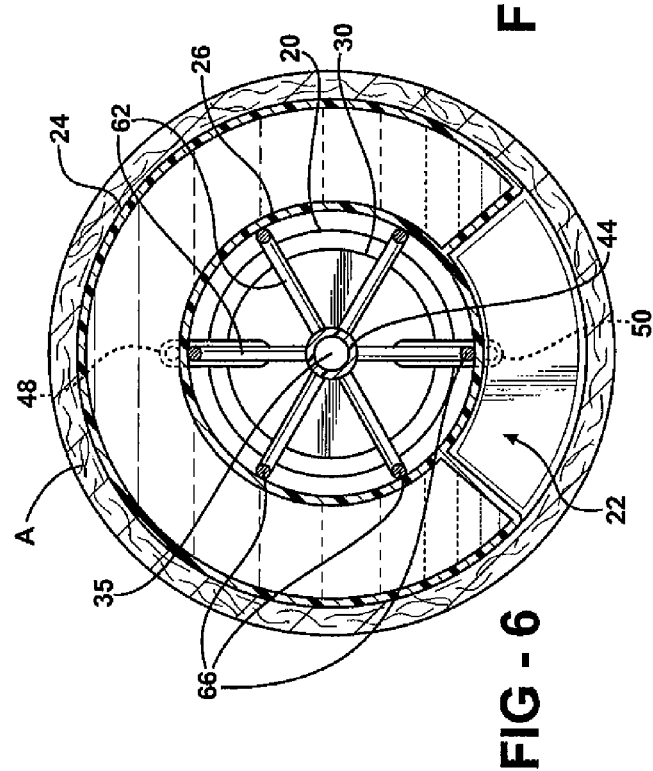

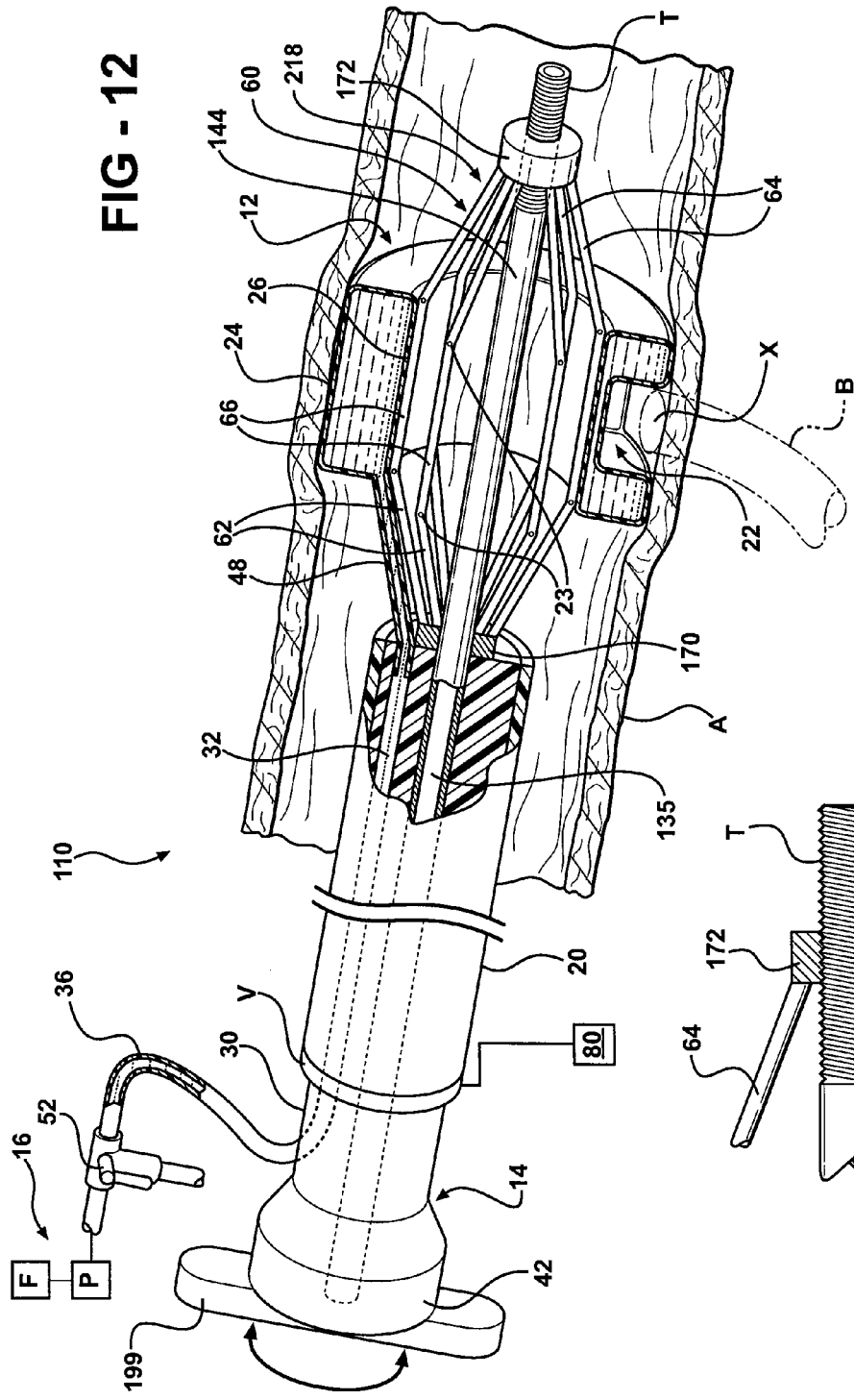

CLAMPLESS ANASTOMOTIC DEVICE

RELATED APPLICATIONS

This application claims the benefit of U.S. Provisional Patent Application Ser. No. 60/910,838, filed on Apr. 10, 2007, the advantages and disclosure of which are hereby incorporated by reference in their entirety.

FIELD OF THE INVENTION

The present invention generally relates to a medical device used in vascular surgery and methods of use thereof. More specifically, the medical device is configured for endoluminal placement within a blood vessel, such as the thoracic or abdominal aorta, via remote arterial access. The medical device provides a working space in the blood vessel that is free of blood flow while still maintaining significant blood flow through the blood vessel. This is particularly useful in performing an aortic anastomosis.

BACKGROUND OF THE INVENTION

Various methods have been developed to revascularize diseased or occluded branches of the aorta. Direct reconstruction via bypass originating from the aorta proximally and anastomosed distally to the artery of interest currently necessitates clamping and partial or total occlusion of the aorta. This interruption of aortic blood flow increases stress on the heart, potentially causing cardiac morbidity. Such occlusion of blood flow inevitably leads to ischemia of downstream organs and extremities, which potentially leads to other complications. Because the aorta itself is often diseased, with varying degrees of calcification within its wall, the act of placing occlusive clamps across the aorta risks injuring the aorta. In addition, plaque within the wall is potentially liberated to embolize distally, which is undesirable.

Numerous devices have been developed to avoid the use of clamps. These devices include various configurations of balloons, cannulae, and perfusion lumens that facilitate anastomosis of a bypass artery to an aorta without aortic clamping. Such devices are disclosed in U.S. Pat. No. 6,695,810 to Peacock et al.; U.S. Pat. No. 6,135,981 to Dyke; U.S. Pat. No. 6,143,015 to Nobles; and U.S. Pat. No. 6,045,531 to Davis. Some of these devices also facilitate "beating heart" bypass procedures in which some blood flow is maintained through the aorta to reduce the risks of complete blood flow occlusion. However, these devices are designed to facilitate coronary artery bypass, and are not suited to other non-coronary applications.

Maintenance of blood flow through the aorta during bypass procedures is important for several reasons. For instance, the avoidance of aortic clamping might allow more laparoscopic aortic procedures. Conventional operations to revascularize branch aortic vessels involve opening the chest or abdomen to allow direct exposure of the vasculature. These large incisions potentially lead to numerous complications, morbidity, or significant loss of body heat. Laparoscopic surgery via very small incisions avoids many of the disadvantages of conventional surgical exposures. It is used commonly in gastrointestinal, gynecologic, thoracic and urologic procedures, yet is not currently applied often to vascular operations. One reason for its sparse use is the current necessity for lengthy aortic occlusion times caused by conventional devices.

Therefore, there is a need in the art for a device and associated methods that facilitate the selective occlusion of blood flow in a working space, while maintaining blood flow through the aorta to allow less morbid arterial revascularizations.

SUMMARY OF THE INVENTION AND ADVANTAGES

The present invention provides a device for selectively occluding blood flow at a target site in a blood vessel while maintaining blood flow through the blood vessel. The device comprises an elongated member and an occlusion structure carried by the elongated member. The occlusion structure includes an occluding member operable between an occluding configuration and a non-occluding configuration. The occluding member defines a working space adapted to be free of blood flow when in the occluding configuration at the target site. The occlusion structure also includes a strut assembly operable between a collapsed and an expanded configuration. The strut assembly carries the occluding member into position at the target site. The strut assembly also defines a flow passage for allowing blood flow therethrough in the expanded configuration at the target site.

In one aspect of the invention, the occluding member is an inflatable member operable between an inflated configuration (corresponds to the occluding configuration) and an un-inflated configuration (corresponds to the non-occluding configuration).

The present invention also provides a method of selectively occluding blood flow at a target site in the thoracic or abdominal aorta while maintaining blood flow through the aorta. The method includes delivering the occluding member and the strut assembly through a remote peripheral artery to the target site in the thoracic or abdominal aorta. Once at the target site, the strut assembly is expanded to open the flow passage. Furthermore, the occluding member contacts the inner wall of the aorta and occludes blood flow in a working space at the target site while maintaining blood flow through the flow passage of the strut assembly.

The present invention provides many advantages over the prior art. For instance, utilizing the strut assembly to support the occluding member provides the required occlusion of blood flow in the working space, while providing a large flow passage therethrough to allow blood flow to continue in the aorta during an anastomosis. More specifically, the strut assembly provides an open-framed support structure that invites blood flow therethrough while supporting the occluding member against the wall of the aorta.

The present invention allows more blood to flow beyond the target site, e.g., the anastomotic region, placing less "afterload" resistance on cardiac output, which will translate into greater utility in fragile patients. The volume of blood flow allowed through the flow passage defined by the expanded strut assembly is significantly greater than that allowed by prior designs.

Additionally, the methods of the present invention provide placement of the device through a remote femoral or brachial access, using percutaneous techniques or small incisions. The device replaces two occlusion clamps, allowing and facilitating minimally-invasive techniques. In addition, by avoiding the ischemia of aortic clamping, anastomoses of longer duration will be tolerable by patients. These longer durations will be necessary with laparoscopic suturing, or with the training of new surgeons.

BRIEF DESCRIPTION OF THE SEVERAL VIEWS OF THE DRAWINGS

Advantages of the present invention will be readily appreciated as the same becomes better understood by reference to the following detailed description when considered in connection with the accompanying drawings wherein:

FIG. 2 is a perspective view of distal end of the device illustrating an inflated balloon mounted to the strut assembly;

FIG. 3 is a cross sectional view taken along line 3-3 in FIG. 1;

FIG. 4 is a cross sectional view taken along line 4-4 in FIG. 1;

FIG. 5 is a cross sectional view taken along line 5-5 in FIG. 1;

FIG. 6 is a cross sectional view taken along line 6-6 in FIG. 1;

FIG. 7 is a cross sectional view taken along line 7-7 in FIG. 1;

FIG. 11 is a perspective view of an alternative helical strut assembly;

FIG. 12 is a perspective, partially schematic, and partially cross-sectional view of yet another embodiment of the device adapted for isolating a segment of an aortic wall from circulation, while allowing blood flow through its center;

FIG. 12A is an elevational and partially cross-sectional view of a tubular support member illustrating threads on the tubular member and corresponding threads on a distal connector or ring;

DETAILED DESCRIPTION OF THE INVENTION

Figure 1:
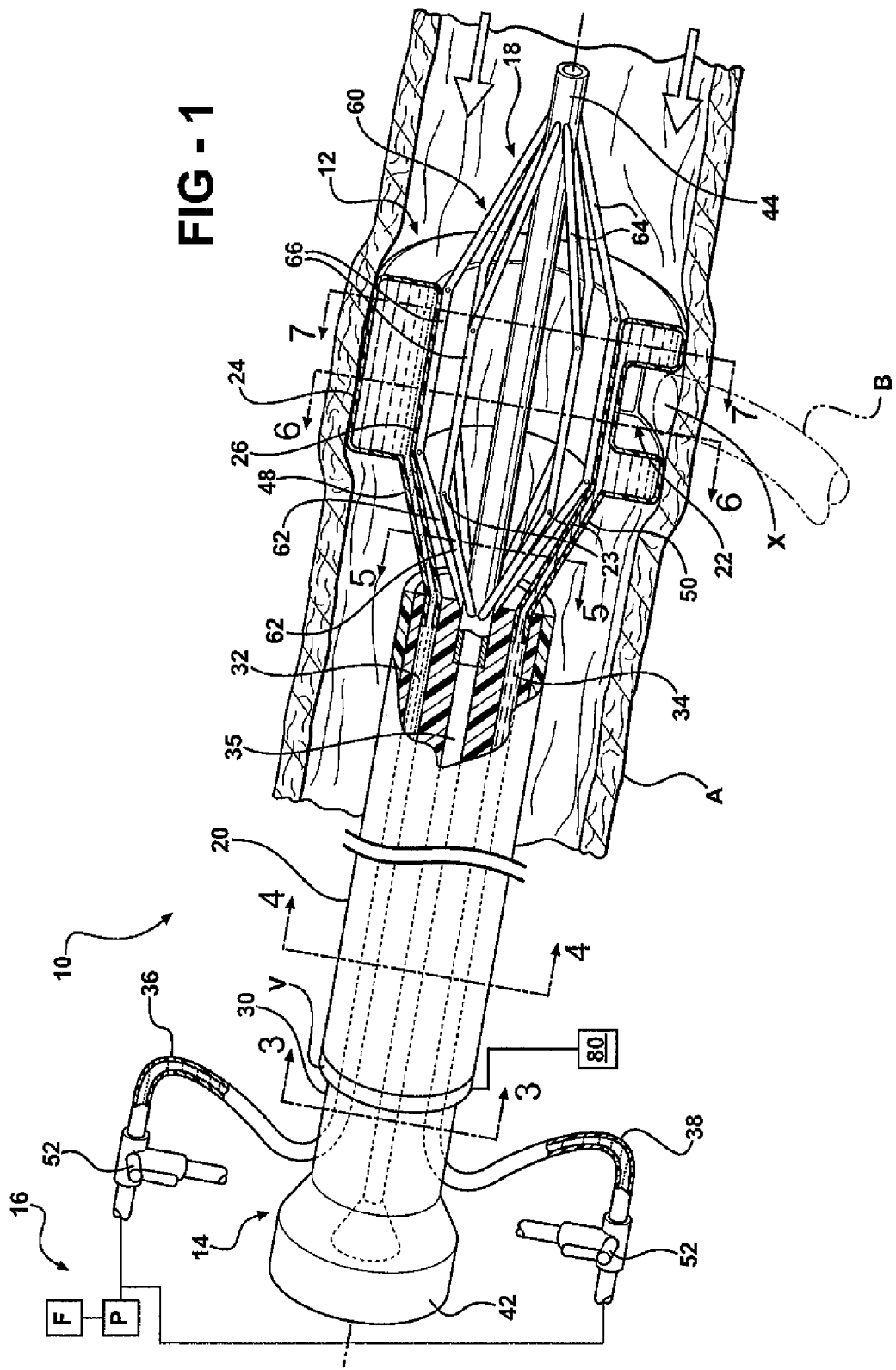
FIG. 1 is a perspective, partially schematic, and partially cross-sectional view of a device adapted for isolating a segment of an aortic wall from circulation, while allowing blood flow through its center.

Referring to the Figures, wherein like numerals indicate like or corresponding parts throughout the several views, a device adapted for selectively occluding blood flow at a target site in a blood vessel while still maintaining blood flow through the blood vessel is generally shown at 10. The device 10 is particularly adapted for providing a working space in an aorta that is free of blood flow to perform an anastomosis, while still maintaining a significant amount of blood flow through the aorta. Arrows in FIG. 1 generally indicate blood flow. In FIG. 1, the device 10 is shown occluding blood flow from a target site X in a blood vessel, such as a thoracic or abdominal aorta A, to facilitate an end-to-side anastomosis of another blood vessel B to the aorta A. It should be appreciated that other uses of the device may be contemplated.

Referring to FIGS. 1-9, the device 10 comprises an occluding member 12, a catheter assembly 14 for endolumenal deployment of the occluding member 12, an inflation/deflation apparatus 16 for inflating and deflating the occluding member 12, a strut assembly 18 for supporting and carrying the occluding member 12, and a constraining sheath 20 for guiding deployment of the occluding member 12.

Figure 8:
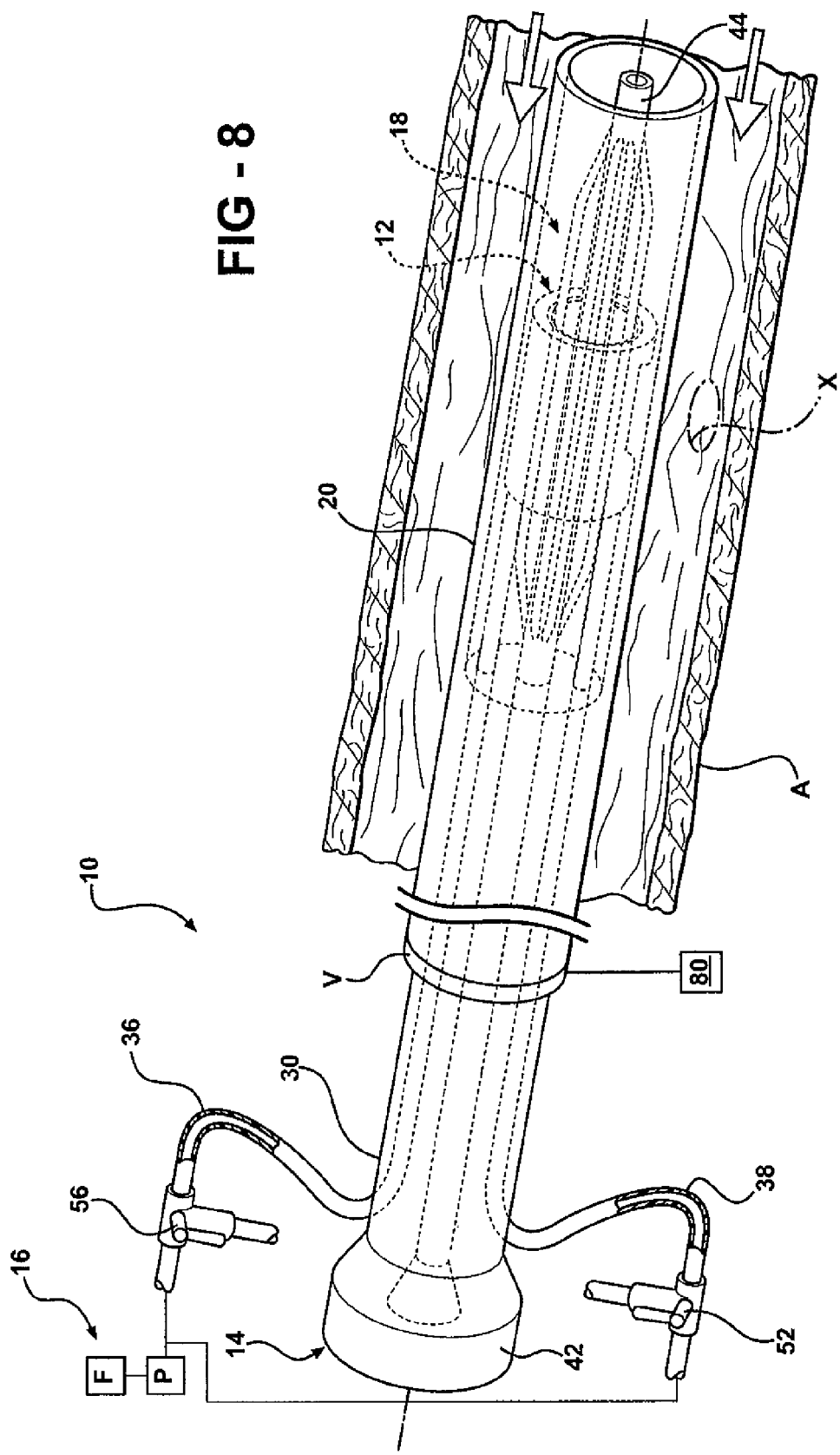
FIG. 8 is a perspective, partially schematic, and partially cross-sectional view of the device in a constrained, balloon-un-inflated configuration with the strut assembly collapsed.
Figure 9:
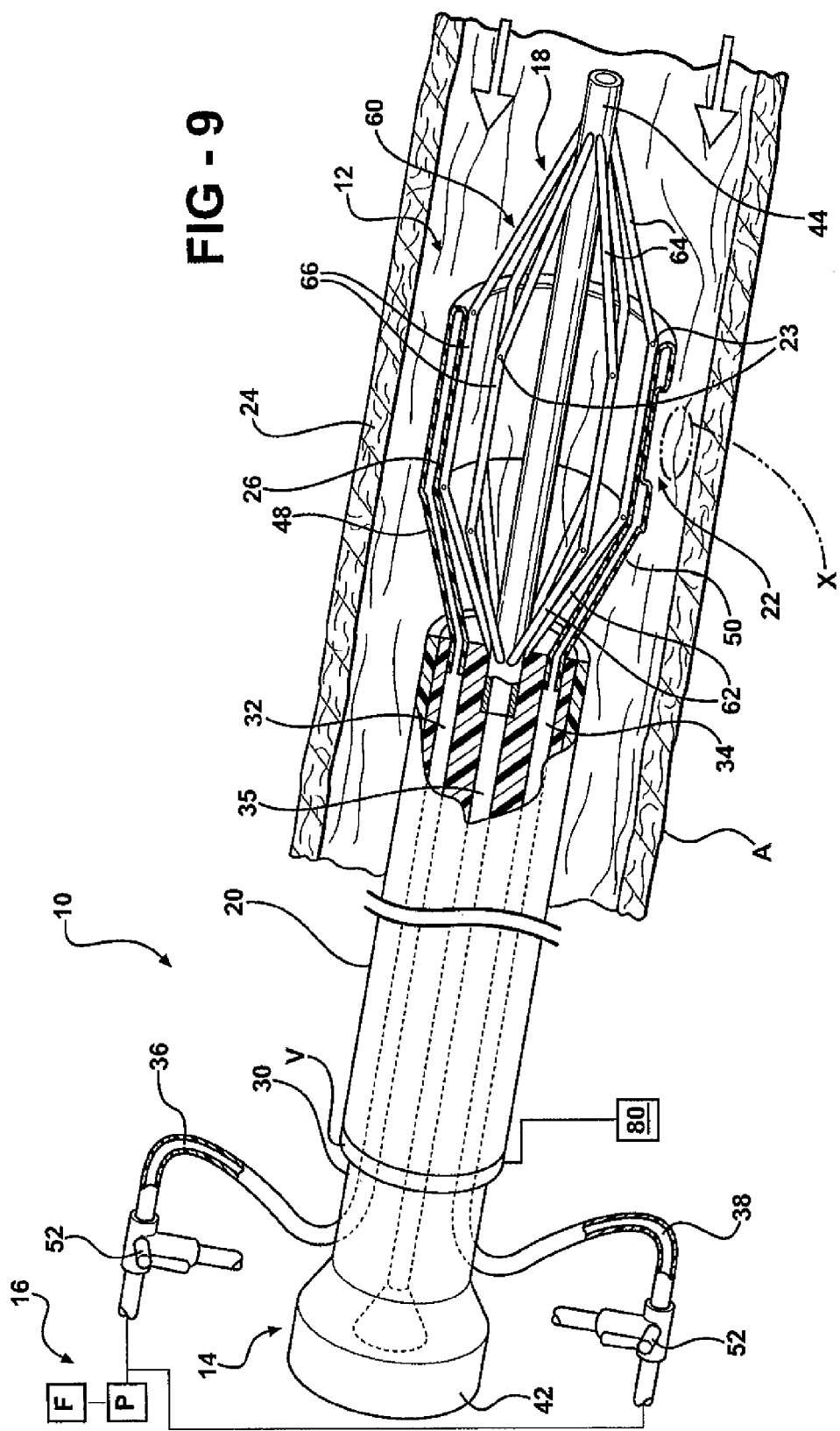
FIG. 9 is a perspective, partially schematic, and partially cross-sectional view of the device in the unconstrained, balloon-un-inflated configuration with the strut assembly expanded.

The occluding member 12 is movable between an occluding configuration, shown in FIG. 1, and a non-occluding configuration, shown in FIGS. 8 and 9. The occluding member 12 is preferably an inflatable member, particularly a balloon 12 operable between inflated and un-inflated configurations. The inflated configuration corresponds to the occluding configuration and the un-inflated configuration corresponds to the non-occluding configuration. One embodiment of the balloon 12 is shown in cross-section in FIG. 1 and in perspective in FIG. 2. When inflated, the balloon 12 contacts an inner surface of the aorta A and seals against the aorta A to prevent blood flow between the balloon 12 and the inner surface of the aorta A. The balloon 12 is generally annular in shape to contact the entire inner surface of the aorta A with the exception of a pocket 22 provided in the balloon 12. The pocket 22 will be variously sized and shaped to accommodate a particular target site X, such as to allow for the standard size and shapes of typical "end-to-side" aortic anastomoses.

In one embodiment, the balloon 12 is formed completely of compliant materials. Preferably, however, the balloon 12 comprises a combination of compliant and non-compliant materials. More specifically, the balloon 12 includes an outer wall 24 comprising an expandable, compliant material that inflates to contact the inner surface of the aorta A and an inner wall 26 comprising a non-compliant material. The pocket 22 is preferably lined on all sides with a non-compliant material so that the sides surrounding the pocket 22 do not expand into the pocket 22. Examples of suitable non-compliant materials include polyethylene terephthalate (PET), nylon, polyetheretherketone (PEEK), and the like. Examples of suitable compliant materials include polyurethane, nylon elastomers, and other thermoplastic elastomers.

Referring to FIG. 2, the balloon 12 is symmetric along its longitudinal axis when cut through the pocket 22. Radiopaque markers 23 are fixed to the balloon 12 at the edges of the pocket 20. These markers 23 allow positioning the balloon 12 within the aorta under fluoroscopy to align the pocket 22 with the optimal position for the anastomosis. The surgeon marks the target site X of the aorta A with metal clips on the aorta's adventitia, or external surface. Under fluoroscopy, the balloon 12 would then be rotated radially and advanced or withdrawn longitudinally to align the pocket 22 with the metal clips. When inflated, the balloon 12 contacts the inner surface of the aorta A and forms lateral seal zones to define the working space for the anastomoses.

Referring back to FIG. 1, the catheter assembly 14 carries the balloon 12 to the target site X for deployment. The catheter assembly 14 includes an elongated member 30 defining a pair of outer lumens 32, 34 and a central guidewire lumen 35. A pair of side ports 36, 38 extends from the elongated member 30. The side ports 36, 38 fluidly communicate with the outer lumens 32, 34 to convey inflation fluid to the balloon 12. The catheter assembly 14 is flexible, yet provides longitudinal stability in the aorta A. A variety of biocompatible polymers, e.g., PVC, polyurethanes, and the like, with or without internal braided metal support, are suitable for forming the catheter assembly 14. The elongated member 30 has a proximal end outfitted with a syringe connector 42, such as a luer-lock connector, to allow preparatory flushing of the guidewire lumen 35.

The catheter assembly 14 further includes a support member in the form of an elongated tube 44 extending distally past a distal end of the elongated member 30. The tube 44 is fixed to the distal end of the elongated member 30. The tube 44 may be fixed to the elongated member 30 by adhesive, ultrasonic welding, press-fit, any combination thereof, or any other suitable manner known to those skilled in the art. The tube 44 is sized such that the guidewire lumen 35 continues beyond the elongated member 30 inside the tube 44 with equal inner diameter such that the guidewire lumen 35 maintains a constant diameter through the elongated member 30 and the tube 44. The tube 44 may comprise the same material as the catheter assembly 14 or may comprise a metal alloy, similar or the same as that used to form the strut assembly 18. In one embodiment, a length of the tube 44 extending beyond the elongated member 30 equals a length of the strut assembly 18 and guides the device 10 over a separate guidewire (not shown).

The catheter assembly 14 further includes a pair of inflation conduits 48, 50 interconnecting the elongated member 30 and the balloon 12. The conduits 48, 50 are preferably cylindrical in shape with a first end fixed to the elongated member 30 at the outer lumens 32, 34 to receive fluid from the outer lumens 32, 34. The conduits 48, 50 extend from the first end to a second end fixed to the balloon 12, e.g., integrally formed with the balloon 12, as shown. The conduits 48, 50 may be fixed to the elongated member 30 and/or balloon 12 by adhesive, ultrasonic welding, press-fit, any combination thereof, or any other suitable manner known to those skilled in the art. The conduits 48, 50 may be seated in counterbores (not shown) in distal end of the elongated member 30 to form an inner diameter matching the diameter of the outer lumens 32, 34. In the embodiment shown, the conduits 48, 50 have a smaller flow diameter than the outer lumens 32, 34.

Two conduits 48, 50 are preferably used for even distribution of inflation fluid during use. In one embodiment, the balloon 12 may be equally divided by a pair of partitions (not shown) into first and second sections, with the second section including the pocket 22. With separate conduits 48, 50, the second section could be inflated first to form the pocket 22 and the first section could then be inflated to ensure a seal against the wall of the aorta A about the target site X. It should be appreciated that in other embodiments a single conduit 48 could be used. In this instance, only one outer lumen 32, and one side port 36 would be necessary to convey fluid to the balloon 12.

The inflation/deflation apparatus 16 comprises a pump P, manual or motorized, that moves inflation fluid through the side ports 36, 38, outer lumens 32, 34, and conduits 48, 50 into the balloon 12. The pump P could be a hand-operated syringe similar to those used in angioplasty procedures, which measure pressure and/or volume of fluid discharged, or a similar motorized pump. The pump P conveys the sterile inflation fluid from an external fluid source F to the balloon 12. The external fluid source F may be a reservoir in the pump P. Each of the side ports 36, 38 includes a three-way stopcock 52 to select between: (1) closing off the side ports 36, 38; (2) opening a fluid path between the fluid source F and the outer lumens 32, 34 to inflate the balloon 12; or (3) opening a fluid path between the outer lumens 32, 34 and atmosphere or a suction source (not shown) to deflate the balloon 12.

Alternative embodiments of the device 10 may include a single external sideport 36 which leads to a single outer lumen 32 that divides within the elongated member 30 to form the two outer lumens 32, 34 (see provisional application incorporated herein by reference). Other embodiments may comprise a single sideport 36 leading to a single outer lumen 34 and a single conduit 48 to the balloon 12. In each of these embodiments, the inflation fluid is pumped from the fluid source F under pressure to inflate the balloon 12.

The strut assembly 18 comprises a plurality of struts 60. In the embodiment shown in FIG. 1, proximal ends of the struts 60 are fixed to the tube 44 at the point where the tube 44 meets the distal end of the elongated member 30. Thus, the tube 44 supports the struts 60. The struts 60 extend to a distal end of the tube 44 and are fixed to the distal end of the tube 44. The struts 60 concentrically support the balloon 12. In one embodiment, six struts 60 equally spaced circumferentially about the tube 44 and radially from the tube 44 are utilized. In other embodiments more or fewer struts 60 may be utilized. The struts 60 may be fixed to the tube 44 by a biocompatible adhesive, ultrasonic welding, metal welding, or other suitable method.

Each of the struts 60 may comprise two angled segments 62, 64 interconnected by a middle segment 66. The angled segments 62, 64 are disposed at an acute angle with respect to a longitudinal axis of the catheter assembly 14. The middle segments 66 are generally parallel to the longitudinal axis of the catheter assembly 14. The proximal angled segments 62 of the struts 60 slope away from the tube 44 for a predetermined distance until the middle segments 66 achieve a suitable diameter for blood flow. The distal angled segments 64 of the struts 60 slope toward the tube 44 until they are fixed to the distal end of the tube 44. The limits of the middle segments 66 are marked by radiopaque markers 23 to allow for positioning of the balloon 12 under fluoroscopy. Cross struts (not shown) could also be used at certain axial positions along the strut assembly 18 to interconnect segments of adjacent struts 60.

Referring to FIG. 5, the conduits 48, 50 are fixed to a pair of opposing struts 60 to support the conduits 48, 50 during endolumenal passage through the aorta A. The conduits 48, 50 may be fixed to these struts 60 by a biocompatible adhesive, ultrasonic welding, or tied by wire or other biocompatible tying material. FIG. 6 illustrates a cross-section of the balloon 12 in its inflated configuration through the pocket 22. FIG. 7 illustrates a cross-sectional view of the inflated balloon 12 in the seal zone formed proximally and distally of the pocket 22. Here, the balloon 12 contacts the inner surface of the aorta A circumferentially, and prevents blood flow into the working space protected by the pocket 22. The shape of the balloon may be designed to minimize the length of this seal zone. The length of the seal zone can be minimized to allow for positioning of the balloon 12 in as many locations as possible without occluding branch blood vessels.

The inner wall 26 of the balloon 12 is attached to the middle segments 66 of the struts 60. The inner wall 26 may be fixed to the middle segments 66 by a suitable adhesive, ultrasonic welding, wire ties, or other biocompatible tying material. In this manner, the strut assembly 18 supports the balloon 12 at the target site X and carries the balloon 12 to the target site X.

The strut assembly 18 is configured to expand from a collapsed configuration to an expanded configuration. In the expanded configuration, the struts 60 provide an open support framework for the balloon 12. This open framework provides suitable support for the balloon 12 during inflation, while allowing significant blood flow therethrough. When the strut assembly 18 is opened to its expanded configuration, a flow passage is opened through the balloon 12 and between the struts 60 to allow blood flow therethrough. At the same time, the pocket 22 provides a working space free of blood flow to allow the anastomosis to be performed. Thus, the balloon 12 and strut assembly 18 together form an occlusion structure that selectively occludes blood flow in the aorta A, without completely stopping blood flow.

The struts 60 are preferably formed from a temperature sensitive shape memory alloy, e.g., nitinol. The struts 60 are preferably formed such that the expanded configuration is their normal configuration. Hence, when the strut assembly 18 is collapsed, a spring bias urges the struts 60 back to their expanded configuration.

In one embodiment shown in FIG. 2, the struts 60 are fixed to proximal 70 and distal 72 connectors, e.g., rings 70, 72, that are mounted about the tube 44. Here, the rings 70, 72 form part of strut assembly 118. The struts 60 can be fixed to the rings 70, 72 by welding. The proximal ring 70 is fixed to the tube 44, e.g., by adhesive, welding, etc., so that the proximal ring 70 cannot move along the tube 44, while the distal ring 72 is slidable along the tube 44. The distal ring 72 is positioned near the distal end of the tube 44 when the strut assembly 118 is in the collapsed configuration, but slides proximally along the tube 44 when the sheath 20 is removed and the struts 60 seek their normally expanded configuration. In this instance, the temperature sensitive shape memory alloy urges the struts 60 into the expanded configuration when the sheath 20 is removed. In other embodiments both rings 70, 72 could be fixed on the tube 44. When both rings 70, 72 are fixed, or when the struts 60 are fixed to the tube 44, the struts 60 can be slightly rotated about the tube 44 to force the struts 60 into the collapsed configuration.

Referring specifically to FIGS. 8 and 9, the sheath 20 is used to constrain the strut assembly 18 and balloon 12 during passage to the target site X and during removal from the target site X after the procedure is complete. An inner diameter of the sheath 20 is selected such that the sheath 20 is easily withdrawn over the un-inflated balloon 12 and the strut assembly 18 to deploy the device 10. The sheath 20 has a distal end shaped to smoothly reconstrain the strut assembly 18 and the deflated balloon 12 upon advancement back over the balloon 12 and the strut assembly 18 when the procedure is completed. To this end, the sheath 20 may include a rounded end, a funnel-shaped end, or the like. The sheath 20 has a proximal end that comprises a hemostatic valve V and aspiration/flush port 80. The hemostatic valve V prevents blood egress around the catheter assembly 14 while in the patient's bloodstream. The flush port 80 allows removal of all air from the sheath 20 prior to its insertion.

Figure 10:
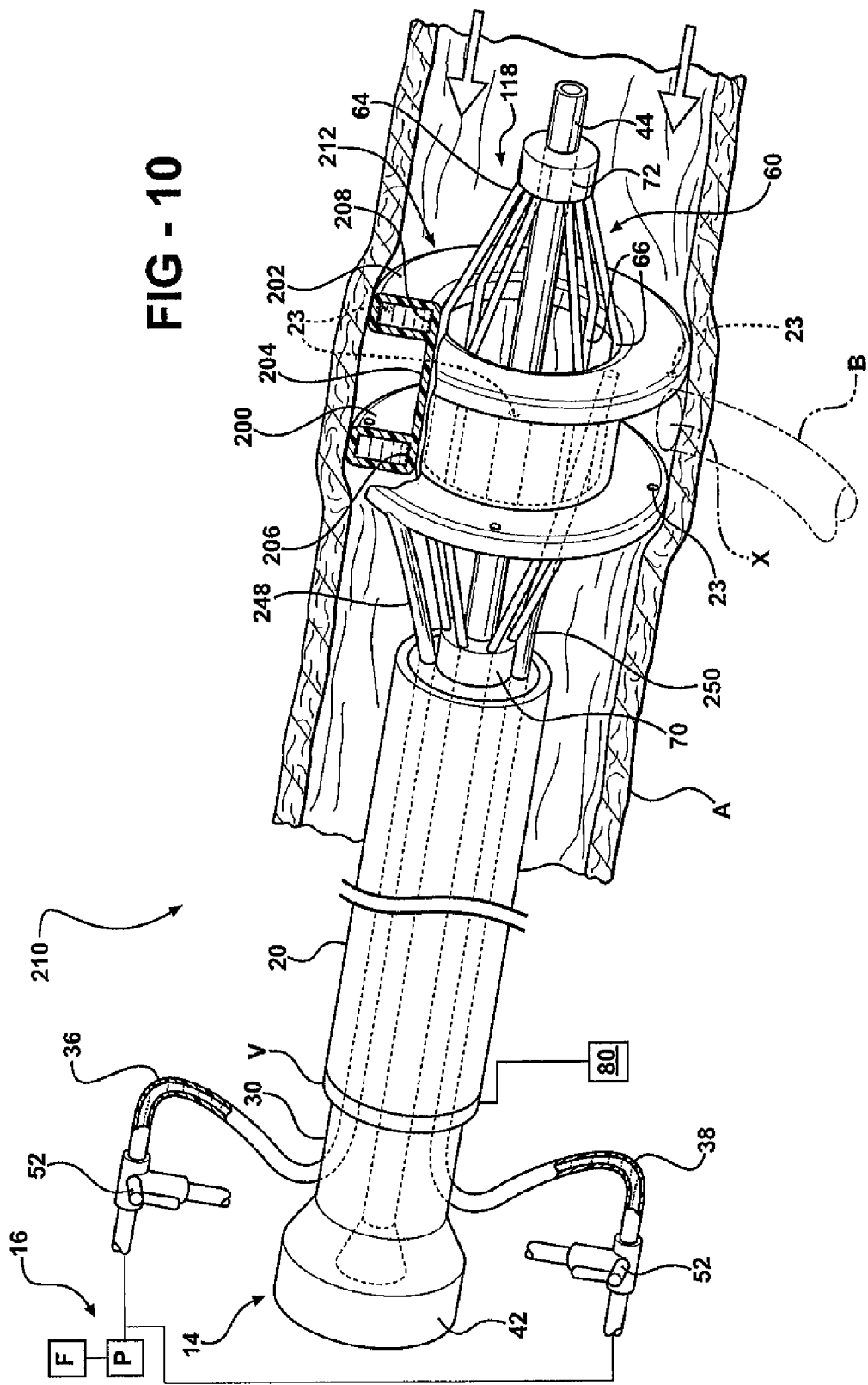
FIG. 10 is a perspective, partially schematic, and partially cross-sectional view of an alternative embodiment of the device adapted for isolating a segment of an aortic wall from circulation, while allowing blood flow through its center.

Referring to FIG. 10, an alternative device 210 is shown. The features of the device 210 are similar to those described above for device 10 so the same reference numerals are used, except that an alternative occluding member 212, e.g., inflatable member 212, is shown. In this alternative, the inflatable member 212 comprises two separate balloons 200, 202 interconnected by a tubular sleeve 204. The sleeve 204 is preferably formed from non-compliant material. The sleeve 204 is fixed to the strut assembly 118 about the middle segments 66, similar to the inner wall 26 of the prior balloon 12. Here, the inner wall 206, 208 of each balloon 200, 202 is fixed to the tubular member 204. As shown, the balloons 200, 202 and sleeve 204 may be integrally formed. The balloons 200, 202 have generally donut shapes. Each of the conduits 248, 250 extends to only one of the balloons 200, 202 to inflate the balloons 200, 202 separately.

Instead of using the pocket 22 to create the working space, which is free of blood flow, the working space is defined between the balloons 200, 202 outside the sleeve 204. The sleeve 204 and strut assembly 118 define the flow passage for blood flow through the aorta A. Radiopaque markers 23 located on the inside surfaces of the balloons 200, 202 again define the limit of the working space. One advantage of this design is avoiding the need for radial orientation of the balloon 200, 202 under fluoroscopy. The conduits 248, 250 would still be fixed to the angled segments 62 of the struts 60, but the distal most conduit 250 would be fixed to an inside portion of the struts 60 to reach the distal balloon 202. In other words, the distal-most conduit 250 would be fixed to a strut 60 of the strut assembly 18 within the flow passage. The balloons 200, 202 are similarly designed to contact the inner surface of the aorta A circumferentially and form the proximal and distal "seal zones" for the working space.

Referring to FIG. 11, another alternative device 310 is shown. In this alternative device 310, an alternative strut assembly 318 is employed. The strut assembly 318 comprises angled strut segments 362, 364, similar to those described above, which expand and collapse to open and close the flow passage for blood flow. The alternative strut assembly 318 can be used with the alternative inflatable member 212 shown in FIG. 10. In this embodiment, the angled segments 362, 364 are interconnected by a plurality of metal wires 300 which expand to define and support the aortic flow channel. The wires 300 are helical in shape to form an expandable stent-like structure, preferably formed of nitinol, which extends between the angled strut segments 362, 364. For instance, if six proximal angled segments 362 and six distal strut segments 364 are used, 6 wires, wound in a helical pattern, interconnect the angled segments 362, 364. The helix structure supports the flow passage in the same manner as illustrated by the longitudinally oriented struts 60 described above. This configuration allows for more flexibility in tortuous vessels.

Figure 13:
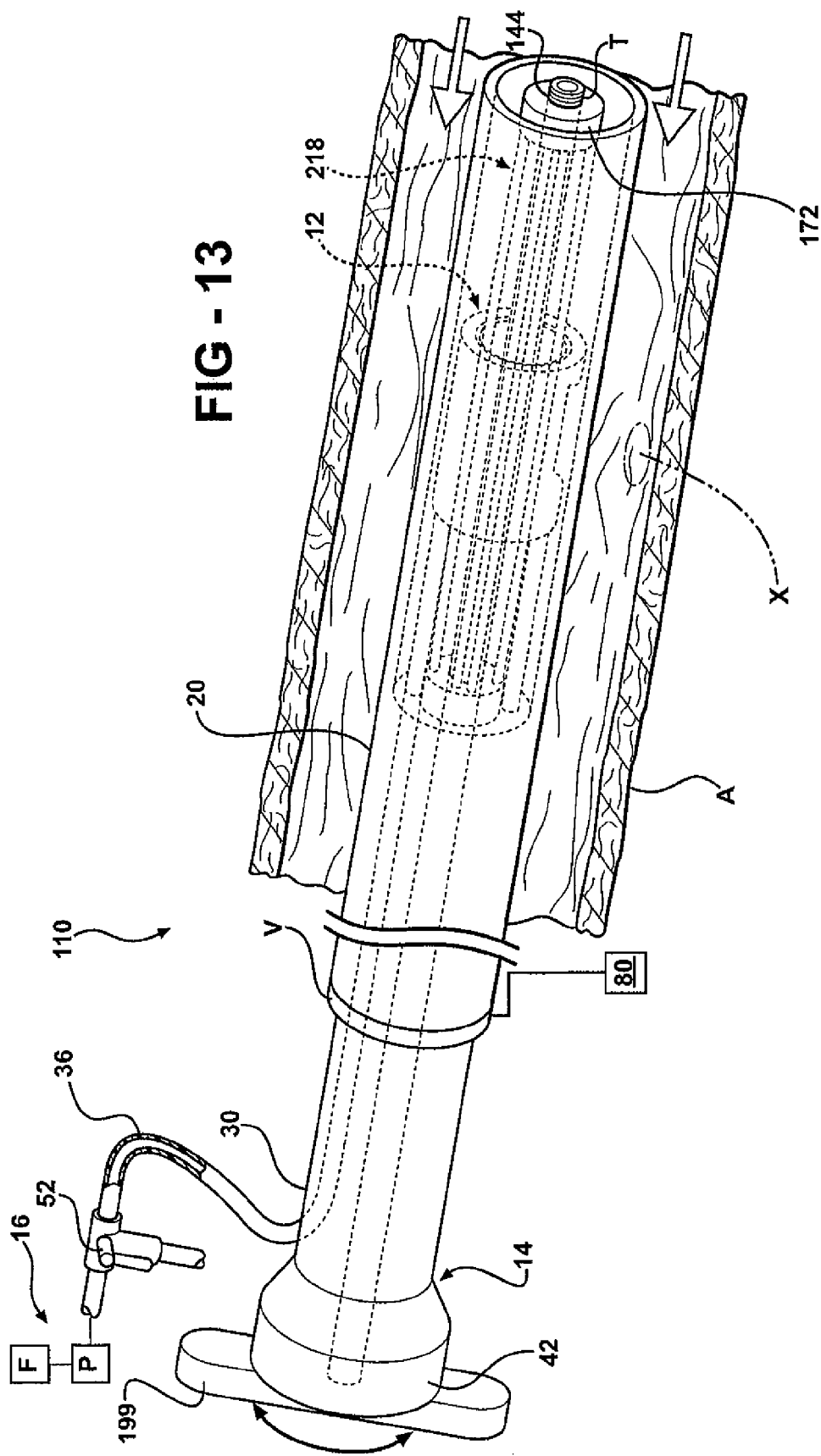
FIG. 13 is a perspective, partially schematic, and partially cross-sectional view of the alternative device of FIG. 12 in the constrained, balloon-un-inflated configuration with the strut assembly collapsed.
Figure 14:
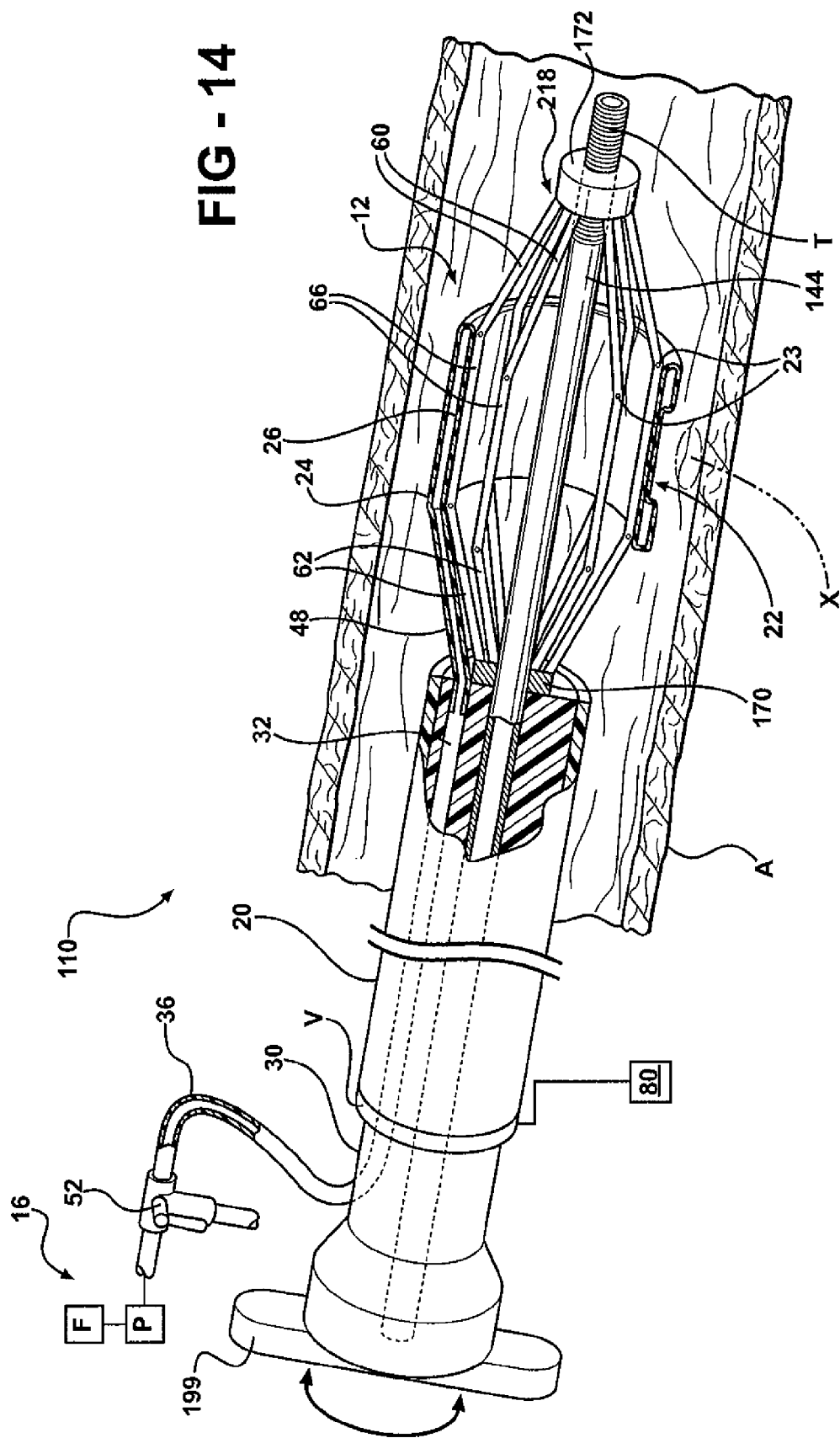
FIG. 14 is a perspective, partially schematic, and partially cross-sectional view of the alternative device of FIG. 12 in the unconstrained, balloon-un-inflated configuration with the strut assembly expanded.

Referring to FIGS. 12-14, yet another alternative device 110 is shown in which the support member, e.g., tube 144, passes entirely through the guidewire lumen 35 to extend both proximally and distally beyond the elongated member 30. Thus, the tube 144 defines a second guidewire lumen 135 of the device 110. In this embodiment, the tube 144, which may be formed of metal or plastic materials, or combinations thereof, is free to rotate relative to the elongated member 30. The internal surface of the distal ring 172 is threaded to match threads T on an external surface of a portion of the tube 144. The portion of the tube 144 with threads T (e.g., the portion distal to the elongated member 30) may be formed of a more rigid material than the remainder of the tube 144, for flexibility during insertion. The proximal ring 170 is fixed to the elongated member 30 by adhesive or the like, and not the tube 144, so that the tube 144 can rotate within the proximal ring 170. The rings 170, 172 and struts 60 form strut assembly 218. The struts 60 are fixed to the rings 170, 172.

A handle 199 is fixed to the proximal end of the tube 144, by adhesive, press-fit, integrally molded therewith, or the like. The handle is rotatable relative to the elongated member 30 and abuts the proximal end of the elongated member 30. The handle 199 has a throughbore (not shown) in communication with the second guidewire lumen 135 for receiving a guidewire (not shown). An operator rotates the tube 144 via the handle 199 to thread the tube 144 in the distal ring 172 (distal ring 172 acts as a nut). At the same time, the operator holds the elongated member 30 from movement. The distal ring 172 is prevented from rotation by the struts 60 (via fixed proximal ring 170), and since the handle 199 abuts the elongated member 30, the tube 144 is restrained at its proximal end from longitudinal movement toward the strut assembly 218. Thus, when the handle 199 and tube 144 rotate relative to the elongated member 30 and the strut assembly 218, the distal ring 172 moves either proximally or distally to expand or collapse the strut assembly 218. In this manner, the struts 60 may be formed of materials other than shape memory alloys. Rotations of the handle 199 can be counted to determine the diameter of the flow passage created.

In other embodiments, the operator could simply pull the handle 199 with the proximal end of the tube 144 fixed thereto to expand the strut assembly 218 and push the handle 199 to collapse the strut assembly 218. In one embodiment (not shown), the external portion of the tube 144 that extends proximally from the elongated member 30 is calibrated and labeled to designate the diameter of the flow passage created. An external lock (not shown), such as a clamp placed on the tube 144 in abutment with the proximal end of the elongated member 30, holds the strut assembly 218 in its expanded position for balloon inflation.

During use, the device 10, 110, 210, 310 is introduced into the body with the strut assembly 18, 118, 218, 318 in its collapsed configuration and the balloon 12, 200, 202 in its un-inflated configuration. In this configuration, the diameter of the device 10, 110, 210, 310 is minimized and allows introduction via the patient's peripheral arteries to the aorta A. The sheath 20 is first inserted through the peripheral artery to the target site X in the aorta A using techniques well known to those skilled in the art.

The catheter assembly 14, carrying the strut assembly 18, 118, 218, 318 and the balloon 12, 200, 202, is then inserted through the sheath 20 to the target site X. FIGS. 8 and 13 show the catheter assembly 14 inside the sheath 20 prior to deployment of the strut assembly 18, 218 and the balloon 12. Once at the target site X, the sheath 20 is withdrawn along the catheter assembly 14 to expose the balloon 12, 200, 202 and the strut assembly 18, 118, 218, 318. As a result, the strut assembly 18, 118, 318 returns to its normally expanded configuration under the spring bias of the struts 60. Alternatively, the strut assembly 218 is placed in its expanded configuration by rotating the handle 199 in the appropriate direction. See, e.g., FIGS. 9 and 14.

The balloon 12, 200, 202 is then inflated such that the outer wall 24 contacts the inner surface of the aorta A to occlude blood flow in the working space. Blood flow then continues through the flow passage located centrally through the balloon 12, 200, 202 and provided by the open framework of the strut assembly 18, 118, 218, 318. Once the procedure is completed, the balloon 12, 200, 202 is deflated and the strut assembly 18, 118, 218, 318 and balloon 12, 200, 202 are re-constrained by the sheath 20 either by pulling the catheter assembly 14 relative to the sheath 20 or by pushing the sheath 20 onto the balloon 12, 200, 202 and strut assembly 18, 118, 218, 318. In the embodiment of FIGS. 12-14, the strut assembly 218 is collapsed by rotating the handle 199 prior to re-constraining the sheath 20 and strut assembly 218.

With the devices 10, 110, 210, 310 of the present invention, blood flow through the vessel (e.g., aorta A) can be maintained while providing the working space at the target site X that is free of blood flow. Preferably, the devices 10, 110, 210, 310 are designed to maximize the area of the flow passage created through the occluding member 12, 212 and strut assembly 18, 118, 218, 318. Preferably, the flow passage has an area (defined in cross-section perpendicular to the vessel) that is at least 20 percent of the original blood flow area of the vessel defined prior to placement of the device 10, 110, 210, 310. More preferably, the flow passage has an area that is at least 35 percent of the original blood flow area of the vessel. Most preferably, the flow passage has an area that is at least 50 percent of the original blood flow area of the vessel.

The invention has been described in an illustrative manner, and it is to be understood that the terminology used is intended to be in the nature of words of description rather than of limitation. As is now apparent to those skilled in the art, many modifications and variations of the present invention are possible in light of the above teachings. For instance, the device 10, 110, 210, 310 could be used for performing angioplasty of the aorta. In this instance, the steps described above are still utilized, except that now the target site X is a stenotic segment formed from build up of cholesterol-laden plaques such as those common to atherosclerosis. The balloon 12, 200, 202 is inflated to expand the stenotic segments and further open blood vessels to the flow of blood.

What is claimed is:

1. A device for selectively occluding blood flow at a target site in a blood vessel while maintaining blood flow through the blood vessel, said device comprising:
   a catheter assembly; and
   an occlusion structure carried by said catheter assembly, said occlusion structure including:
      an inflatable member operable between an inflated configuration and an un-inflated configuration, said inflatable member defining a working space and being adapted to seal against a wall of the blood vessel to provide a barrier that encloses said working space to isolate said working space from the blood flow when in said inflated configuration at the target site; and
      a strut assembly having a proximal end and a distal end with said catheter assembly having a support member extending through said strut assembly, said strut assembly operable between a collapsed configuration and an expanded configuration independent of said inflated and un-inflated configurations of said inflatable member, said strut assembly carrying said inflatable member and defining a flow passage between said support member and said inflatable member for allowing blood flow therethrough in said expanded configuration at the target site.

2. A device as set forth in claim 1 including a sheath slidable relative to said catheter assembly between a first position constraining said strut assembly in said collapsed configuration and a second position releasing said strut assembly to allow said strut assembly to expand from said collapsed configuration to said expanded configuration.

3. A device as set forth in claim 1 wherein said inflatable member has an outer wall and an inner wall mounted to said strut assembly.

4. A device as set forth in claim 3 wherein said outer wall of said inflatable member is formed of a first material and said inner wall of said inflatable member is formed of a second material that is non-compliant relative to said first material.

5. A device as set forth in claim 1 wherein said inflatable member is further defined as a balloon with a pocket to define said working space.

6. A device as set forth in claim 1 wherein said inflatable member is defined as a pair of balloon portions interconnected by a sleeve.

7. A device as set forth in claim 1 wherein said catheter assembly is adapted to carry said occlusion structure through a femoral or brachial artery to the target site in an aorta while said inflatable member is in said un-inflated configuration and said strut assembly is in said collapsed configuration.

8. A device as set forth in claim 1 including an inflation mechanism for inflating said inflatable member to occlude blood flow in said working space while maintaining blood flow through said flow passage.

9. A device as set forth in claim 1 wherein said strut assembly is normally biased toward said expanded configuration.

10. A device as set forth in claim 1 wherein said strut assembly includes a plurality of struts.

11. A device as set forth in claim 10 wherein each of said plurality of struts are at least partially formed of a shape memory alloy.

12. A device as set forth in claim 11 wherein each of said plurality of struts are formed of nitinol.

13. A devices as set forth in claim 10 wherein said catheter assembly includes an elongated member with said support member extending distally from said elongated member, said support member supporting said plurality of struts.

14. A device as set forth in claim 13 wherein said strut assembly includes proximal and distal connectors with each of said plurality of struts extending between said connectors.

15. A devices as set forth in claim 14 wherein said support member is further defined as an elongated tube having a threaded portion with at least one of said connectors having corresponding threads for mating engagement therewith.

16. A device as set forth in claim 15 wherein said proximal connector is fixed from movement relative to said elongated member and said distal connector is movable relative to said elongated member.

17. A device as set forth in claim 1 including a plurality of radiopaque markers mounted to said inflatable member for determining the orientation of said inflatable member.

18. A device as set forth in claim 1 wherein said catheter assembly extends through said inflatable member with said flow passage defined between said catheter assembly and said inflatable member.

19. A device as set forth in claim 1, further comprising separate conduits in fluid communication with independently inflatable sections of said inflatable member for independently inflating said sections.

20. A device as set forth in claim 1 further comprising a partition separating independently inflatable sections of said inflatable member.

21. An occlusion structure for selectively occluding blood flow at a target site in a blood vessel while maintaining blood flow through the blood vessel, said structure comprising:

an inflatable member operable between an un-inflated configuration and an inflated configuration, said inflatable member defining a working space and being adapted to seal against a wall of the blood vessel to provide a barrier that encloses said working space to isolate said working space from the blood flow when in said inflated configuration at the target site; and a strut assembly having a proximal end and a distal end with a catheter assembly having a support member extending through said strut assembly, said strut assembly operable between a collapsed configuration and an expanded configuration independent of said inflated and un-inflated configurations of said inflatable member, said strut assembly supporting said inflatable member and defining a flow passage between said support member and said inflatable member for allowing blood flow therethrough in said expanded configuration at the target site.

22. A method of selectively occluding blood flow at a target site in a thoracic or abdominal aorta while maintaining blood flow through the aorta, said method comprising the steps of:

providing a catheter assembly;

providing an inflatable member operable between an inflated configuration and an un-inflated configuration;

providing a strut assembly having a proximal end and a distal end with the catheter assembly having a support member extending through the strut assembly, the strut assembly operable between a collapsed configuration and an expanded configuration independent of the inflated and un-inflated configurations of the inflatable member, the strut assembly supporting the inflatable member and defining a flow passage between the support member and the inflatable member for allowing blood flow therethrough the expanded configuration;

delivering the inflatable member and the strut assembly through a remote peripheral artery to the target site in the thoracic or abdominal aorta;

expanding the strut assembly once at the target site to open the flow passage; and moving the inflatable member once at the target site to contact a wall of the aorta and occlude blood flow in the working space at the target site while maintaining blood flow through the flow passage.

\* \* \* \* \*